United States Patent
Andreyev et al.

(10) Patent No.: US 12,131,410 B2
(45) Date of Patent: Oct. 29, 2024

(54) EDGE PRESERVING PENALIZED RECONSTRUCTION FOR STEP-AND-SHOOT AND MOTION COMPENSATED POSITRON EMISSION TOMOGRAPHY (PET) STUDIES

(71) Applicant: KONINKLIJKE PHILIPS N.V., Eindhoven (NL)

(72) Inventors: Andriy Andreyev, Willoughby Hills, OH (US); Xiyun Song, Cupertino, CA (US); Ravindra Mohan Manjeshwar, Solon, OH (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 577 days.

(21) Appl. No.: 17/293,958

(22) PCT Filed: Nov. 15, 2019

(86) PCT No.: PCT/EP2019/081515
§ 371 (c)(1),
(2) Date: May 14, 2021

(87) PCT Pub. No.: WO2020/099649
PCT Pub. Date: May 22, 2020

(65) Prior Publication Data
US 2022/0012928 A1     Jan. 13, 2022

Related U.S. Application Data

(60) Provisional application No. 62/768,131, filed on Nov. 16, 2018.

(51) Int. Cl.
*G06T 11/00* (2006.01)
*A61B 6/03* (2006.01)

(52) U.S. Cl.
CPC ............ *G06T 11/008* (2013.01); *A61B 6/037* (2013.01); *G06T 11/006* (2013.01); *G06T 2211/424* (2013.01)

(58) Field of Classification Search
CPC ...... G06T 11/008; G06T 11/006; G06T 11/00; G06T 2211/424; A61B 6/037
See application file for complete search history.

(56) References Cited

U.S. PATENT DOCUMENTS

| | | | |
|---|---|---|---|
| 2006/0081784 A1* | 4/2006 | Ross | G06T 11/006 250/363.03 |
| 2009/0123048 A1 | 5/2009 | Leroux | |

(Continued)

FOREIGN PATENT DOCUMENTS

| | | |
|---|---|---|
| WO | 2017174627 A1 | 10/2017 |
| WO | 2018108848 A1 | 6/2018 |

OTHER PUBLICATIONS

Wang et al, Penalized Likelihood PET Image Reconstruction using Patch-based Edge-preserving Regularization, IEEE Trans Med Imaging, 31(12): 2194-2204, pp. 1-29. (Year: 2012).*

(Continued)

*Primary Examiner* — Aaron W Carter
*Assistant Examiner* — Kathleen M Broughton

(57) ABSTRACT

A non-transitory computer-readable medium stores instructions readable and executable by a workstation (18) including at least one electronic processor (20) to perform an imaging method (100). The method includes: receiving imaging data on a frame by frame basis for frames along an axial direction with neighboring frames overlapping along the axial direction wherein the frames include at least a volume (k) and a succeeding volume (k+1) at least partially overlapping the volume (k) along the axial direction; and generating an image of the volume (k) using an iterative image reconstruction process in which an iteration of the (Continued)

iterative image reconstruction process includes: computing a local penalty function for suppressing noise over the volume (k) including reducing the value of the local penalty function in an overlap region; generating an update image of the volume (k) using imaging data from the volume (k) and further using the local penalty function.

15 Claims, 4 Drawing Sheets

(56) References Cited

U.S. PATENT DOCUMENTS

| | | | |
|---|---|---|---|
| 2013/0182930 A1* | 7/2013 | Trzasko | G06T 11/006 |
| | | | 382/131 |
| 2014/0126793 A1 | 5/2014 | Ahn | |
| 2014/0161340 A1 | 6/2014 | Zeng | |
| 2015/0117733 A1* | 4/2015 | Manjeshwar | G06T 11/003 |
| | | | 382/131 |
| 2015/0256735 A1 | 9/2015 | Barkan | |
| 2015/0363948 A1* | 12/2015 | Leahy | A61B 6/504 |
| | | | 600/425 |
| 2016/0063741 A1 | 3/2016 | Ye | |
| 2016/0174919 A1* | 6/2016 | Ahn | G06T 7/0012 |
| | | | 382/131 |
| 2016/0225169 A1* | 8/2016 | Bippus | G06T 11/005 |
| 2017/0053423 A1 | 2/2017 | Ahn | |
| 2017/0061629 A1* | 3/2017 | Zhu | G06T 11/008 |
| 2017/0103551 A1 | 4/2017 | Sun | |
| 2017/0249758 A1 | 8/2017 | Mistretta | |
| 2019/0122399 A1* | 4/2019 | Jain | G06T 3/4007 |
| 2020/0294285 A1 | 9/2020 | Song | |

OTHER PUBLICATIONS

International Search Report and Written Opinion of PCT/EP2019/081515, dated Jan. 30, 2020.

Zhu, H. "Image Reconstruction for Positron Emission Tomography using Fussy Nonlinear Anisotropic Diffusion Penalty", Medical and Biology Engineering and Computer, Dec. 2006.

Nuyts, J. et al "A Concave Prior Penalizing relative Differences for Maximum-a-Posteriori Reconstruction in Emission Tomography", IEEE Transactions on Nuclear Science, Mar. 2002.

Ross, S. et al "A Method of Overlap Correction for Fully 3D OSEM Reconstruction of PET Data", MIC 2004.

Salomon, Andre et al Information-Adaptive Regularization for Iterative PET Reconstruction, 2016.

* cited by examiner

EDGE PRESERVING PENALIZED RECONSTRUCTION FOR STEP-AND-SHOOT AND MOTION COMPENSATED POSITRON EMISSION TOMOGRAPHY (PET) STUDIES

CROSS-REFERENCE TO PRIOR APPLICATIONS

This application is the U.S. National Phase application under 35 U.S.C. § 371 of International Application No. PCT/EP2019/081515, filed on Nov. 15, 2019, which claims the benefit of U.S. Provisional Patent Application Ser. No. 62/768,131 filed Nov. 16, 2018. These applications are hereby incorporated by reference herein.

FIELD

The following relates generally to the medical imaging arts, positron emission tomography (PET) imaging and image reconstruction arts, regularized iterative image reconstruction arts, and related arts.

BACKGROUND

Image quality in positron emission tomography (PET) is strongly dominated by noise. Iterative maximum-a-posteriori penalized reconstruction (PR) using an edge-preserving or contrast preserving prior is one approach to suppress noise while retaining small features (e.g. tumors) that may be of clinical interest. Some edge-preserving or contrast preserving penalties include: (1) relative difference penalty (RDP) (see, e.g., J. Nuyts et al., "A concave prior penalizing relative differences for maximum-a-posteriori reconstruction in emission tomography," IEEE Trans. Nucl. Sci., 2002); (2) anisotropic diffusion penalty (ADP) (see, e.g., H. Zhu, "Image reconstruction for positron emission tomography using fuzzy nonlinear anisotropic diffusion penalty," Med Bio Eng Comput, 2006), and so on. In most edge-preserving penalties, a tuning parameter establishes sensitivity to the edge transition in the reconstructed images, and imaging data below the sensitivity threshold is smoothed by a strong low-pass filter.

Commercial PET cameras have a limited axial field of view (FOV) due to the finite axial extent of the PET detector rings or array. Therefore, a "whole body" patient scan is typically acquired in a serial "step-and-shoot" mode at multiple bed positions with certain overlap between the bed positions. For practical reasons, each bed position is typically reconstructed separately without waiting for the PET data for the next bed position to be fully acquired, and the reconstructed individual frame images are knitted into a single whole-body image. Each bed position overlaps to ensure smooth signal transition in the axial direction. Typically, for whole body studies, more than 50% of the scanned axial extent will be covered in overlap slices. Therefore, in every reconstructed image volume, there will be one or two sub-volumes that are covered by the acquired counts from either previous bed position or next bed position (note that, as discussed herein, it is assumed that in all situations considered the number of bed positions is at least larger than one).

Instead of reconstructing each bed position separately and then knitting the images together in image space, in an alternative approach the counts are pre-combined (either in sinogram format or list mode) before the reconstruction without overcomplicating the imaging workflow (see, e.g., Z. Sun, et al. "Reconstruction and combination of PET multi-bed image," US Pub. No. 2017/0103551). However, previous work shows that at least Ordered Subset Expectation Maximization (OSEM) iterative image reconstruction algorithm demonstrates quasi-linear behavior and there is little practical benefit of pre-combining the counts before the reconstruction except for ultra-low count studies (see, e.g., S. Ross et al., "A method of overlap correction for fully 3D OSEM reconstruction of PET data", MIC, 2004). In the case of reconstructing every bed position separately, each bed position image can have noisier appearance in the edge slices due to effective "loss" of data at the edges. But, the noise can generally be compensated during the image knitting procedure (i.e., when the individual bed position images are combined into a single whole-body image).

The following discloses new and improved systems and methods to address these problems.

SUMMARY

In one disclosed aspect, a non-transitory computer-readable medium stores instructions readable and executable by a workstation including at least one electronic processor to perform an imaging method. The method includes: receiving imaging data on a frame by frame basis for frames along an axial direction with neighboring frames overlapping along the axial direction wherein the frames include at least a volume (k) and a succeeding volume (k+1) at least partially overlapping the volume (k) along the axial direction; and generating an image of the volume (k) using an iterative image reconstruction process in which an iteration of the iterative image reconstruction process includes: computing a local penalty function for suppressing noise over the volume (k) including reducing the value of the local penalty function in an overlap region; generating an update image of the volume (k) using imaging data from the volume (k) and further using the local penalty function.

In another disclosed aspect, an imaging system includes a positron emission tomography (PET) imaging device. At least one electronic processor is programmed to: receive imaging data on a frame by frame basis for frames along an axial direction with neighboring frames overlapping along the axial direction wherein the frames include at least a volume (k) and a succeeding volume (k+1) at least partially overlapping the volume (k) along the axial direction; and generate an image of the volume (k) using an iterative image reconstruction process in which an iteration of the iterative image reconstruction process includes: computing a local penalty function for suppressing noise over the volume (k) including reducing the value of the local penalty function in an overlap region, the local penalty function depending on the total coincidence counts passing through the voxel being penalized, and the value of the local penalty function is reduced in the overlap region by an amount compensating for the total coincidence counts passing through the voxel being penalized in the succeeding volume k+1; generating an update image of the volume (k) using imaging data from the volume (k) and further using the local penalty function. The reconstructing includes: combining the number of counts from the volumes (k) in the imaging data into a total volume; and reconstructing the total volume into a reconstructed image.

In another disclosed aspect, an imaging method performed on imaging data on a frame by frame basis for frames along an axial direction with neighboring frames overlapping along the axial direction wherein the frames include at least a volume (k) and a succeeding volume (k+1) at least partially overlapping the volume (k) along the axial direction includes: generating an image of the volume (k) using an iterative image reconstruction process in which an iteration of the iterative image reconstruction process includes: computing a local penalty function for suppressing noise over the volume (k) including reducing the value of the local penalty function in an overlap region, the local penalty function depends on local geometric sensitivity of the PET imaging device and the value of the local penalty function is reduced in the overlap region by an amount compensating for loss of geometric sensitivity due to axial truncation of the volume (k); generating an update image of the volume (k) using imaging data from the volume (k) and further using the local penalty function. The reconstructing includes reconstructing the volume (k) of the imaging data separately from the other volumes (k) of the imaging data into a reconstructed image.

In another disclosed aspect, an imaging method performed on imaging device to acquire imaging data on a frame by frame basis for frames along an axial direction with neighboring frames overlapping along the axial direction wherein the frames include at least a volume (k) and a succeeding volume (k+1) at least partially overlapping the volume (k) along the axial direction includes: generating an image of the volume (k) using an iterative image reconstruction process in which an iteration of the iterative image reconstruction process includes: adjusting the imaging data with respiratory gating using two or more gate phases and motion detected in the gate phases; computing a local penalty function for suppressing noise over the volume (k) including reducing the value of the local penalty function in an overlap region; generating an update image of the volume (k) using imaging data from the volume (k) and further using the local penalty function.

One advantage resides in utilizing all available counts from a PET imaging device to properly adjust parameters of a reconstruction penalty function.

Another advantage resides in providing an edge-preserving penalized reconstruction process that avoids over-smoothing of a final image, leading to potentially lost image features.

Another advantage resides in providing an edge-preserving penalized reconstruction process that avoids under-smoothing of a final image, leading to potential noise in the image.

Another advantage resides in, when data in overlapping regions of imaging data are combined before image reconstruction, reducing a penalty function proportionally to an effective sensitivity increase introduced by combining neighboring images in the overlap region to preserve a spatial resolution of a reconstructed image.

Another advantage resides in, when data in overlapping regions of imaging data are not combined before image reconstruction, reducing a penalty function to preserve a spatial resolution of a reconstructed image.

Another advantage resides in scaling a penalty function with an acquisition duration ratio between two imaging frames.

Another advantage resides in dynamically adjusting penalty parameters of a penalty function with count-end-points-adjusted motion corrected respiratory or cardiac gated or dynamic studies.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The disclosure may take form in various components and arrangements of components, and in various steps and arrangements of steps. The drawings are only for purposes of illustrating the preferred embodiments and are not to be construed as limiting the disclosure.

DETAILED DESCRIPTION

Figure 1:
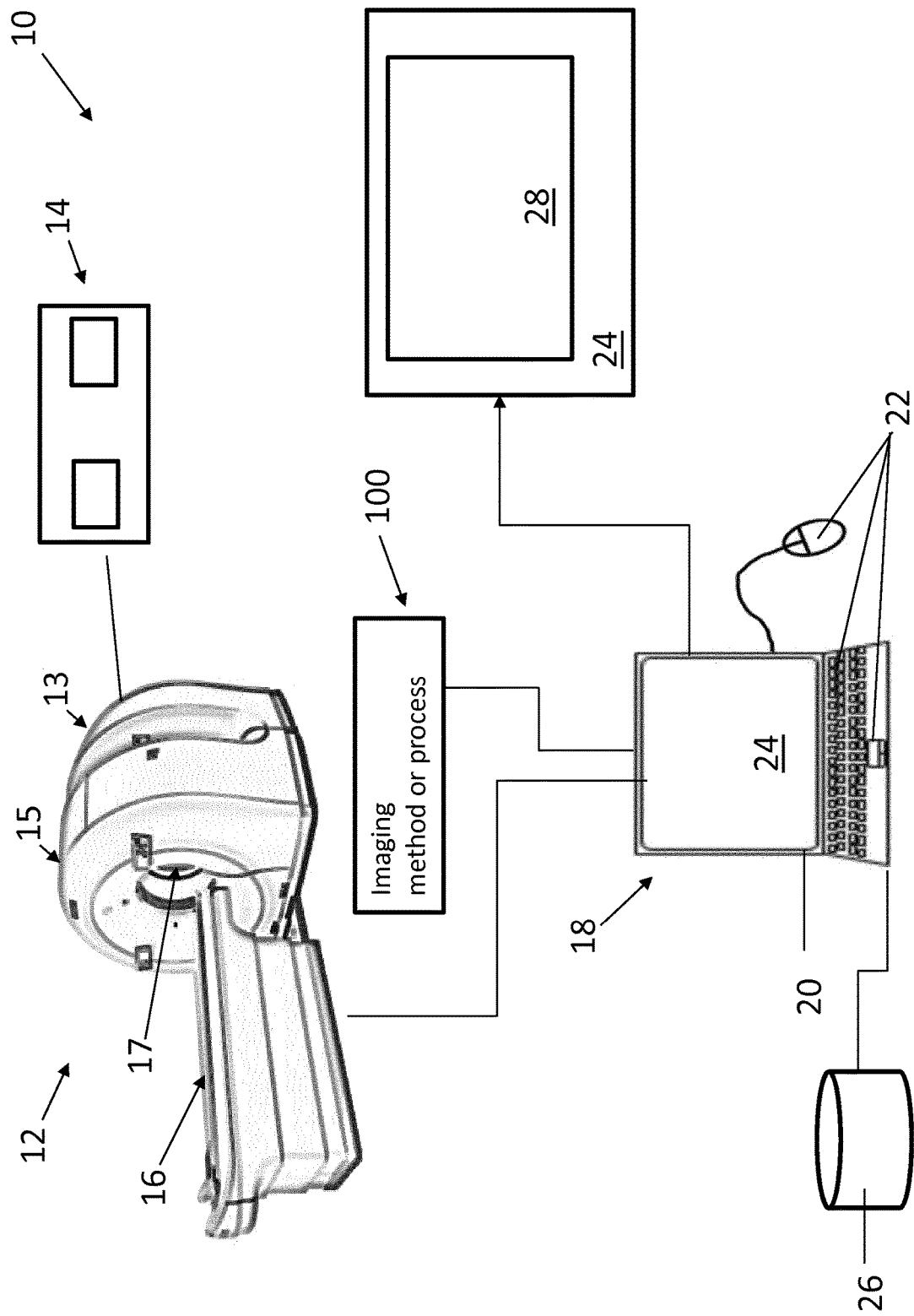
FIG. 1 diagrammatically shows an imaging system according to one aspect.

Iterative penalized PET image reconstruction employs an update function that includes a penalty term designed to penalize (i.e. suppress) noise while retaining edges. For example, a relative difference penalty (RDP) employs a penalty $P \propto 1/\gamma$ where the term $\gamma$ is the edge preservation parameter. Larger values of $\gamma$ produce a smaller penalty P which enhances preservation of features (i.e., "edges") such as small lesions but also leads to retention of more noise; whereas, smaller values of $\gamma$ increase the penalty which improves noise suppression, but can also lead to removal of clinically significant structures (i.e., "edges") such as small lesions. In a variant approach, the penalty is locally tuned, for example by using $\gamma = \sqrt{\lambda_i s_i}$ where $\lambda_i$ is the value of the voxel indexed by i and $s_i$ is the geometric sensitivity at the voxel i which is proportional to the number of lines of response (LORs) passing through the voxel i. This formulation is premised on the expectation that if more LORs pass through the voxel i (hence higher $s_i$) then there should be more counts in the vicinity and hence noise should be lower at voxel i, so that a smaller penalty P can be used to enhance edges while still suppressing the (relatively low) noise. In an alternative tuning, the geometric sensitivity $s_i$ is replaced by a term which quantifies the total counts in a local neighborhood around voxel i. Again, higher total counts in the local neighborhood tends to correspond with lower noise, so that a lower penalty P can be used.

It is recognized herein that such penalization frameworks can be less effective in the case of overlap regions of step-and-shoot PET imaging. In the step-and-shoot approach (also known as multi-bed imaging or similar nomenclatures), the patient is stepped through the scanner to image successive axial portions ("bed positions") of the patient. The data acquired at each bed position is thus axially truncated at edge slices corresponding to the locations of the outermost detector rings of the PET scanner at that bed position. Conventionally, the PET counts acquired at each bed position are separately reconstructed (but possibly using information from neighboring bed positions to estimate out-of-FOV scatter), and the resulting bed position images are knitted together at the overlaps by weighted averaging of the voxel values in the overlapping regions of the bed position images. In such an approach, however, the local tuning of the penalty is computed using geometric sensitivities $s_i$ for that bed position. For outer slices of the bed position, sensitivities $s_i$ become small because the LORs that terminate outside of the axial FOV of the bed position do not contribute to the sensitivity $s_i$. For the extreme edge slices, only LORs that are in the plane of the slice contribute to $s_i$. This means that the penalty $P \propto 1/\gamma = 1/\sqrt{\lambda_i s_i}$ becomes large at the outer slices, leading to excessive noise suppression in the overlap regions and enhance potential for suppression of clinically relevant image features such as small tumors. The subsequent knitting together of adjacent bed position images at the overlap cannot recover these suppressed features, since both overlap regions will have this same "edge effect" in the penalty leading to loss of features. The alternative formulation in which $s_i$ is replaced by the total counts in a local neighborhood is similarly affected since counts are not acquired for LORs that terminate outside the truncated axial FOV of the bed position.

In some disclosed embodiments, the local penalty in the overlap regions is reduced in order to account for the above effect.

In some embodiments disclosed herein, the reduction is proportional to the effective sensitivity increase (or effective total neighborhood counts increase) that would be achieved if the truncated volume k was continued into the adjacent overlapping truncated volume k+1. In one approach employing geometric sensitivity for adjusting the penalty, this amounts to replacing $\gamma_{i,k}^{sep}=\sqrt{\lambda_{i,k}s_{i,k}}$ with $\gamma_{i,k}^{joint}=\sqrt{\lambda_{i,k}(s_{i,k}+s_{i,k+1})}$ in the overlap region, where the $s_{i,k+1}$ term accounts for those LORs that are not part of the volume k (and hence do not contribute to geometric sensitivity $s_{i,k}$) but are part of the overlapping volume k+1 (and hence contribute to the geometric sensitivity $s_{i,k+1}$). A similar formulation can be used if locally adjusting γ using the total counts in a local neighborhood, by employing a summation of the total counts in the neighborhood of voxel i from both overlapping volumes k and k+1.

In the above embodiment, each volume k is still reconstructed separately. In an alternative joint reconstruction embodiment, the PET counts from all volumes is first combined and then reconstructed together. In this case $\gamma_{i,k}^{joint}$ is again used. Here a suitable formulation could be $\gamma_i^{joint}=\sqrt{\lambda_i(s_{i,k}+s_{i,k+1})}$ where $\lambda_i$ is the value of voxel i produced by the (single) joint reconstruction of the combined data set.

In a variant embodiment, if acquisition times for the various bed positions are different then the sensitivities $s_{i,k}$ and $s_{i,k+1}$ are scaled proportionally to the acquisition times. This is due to a lower acquisition time resulting in fewer counts being acquired and correspondingly lower sensitivity. So, if the acquisition times are $T_k$ and $T_{k+1}$ for respective overlapping bed positions k and k+1 then the scaling is $$s_{i,k} \to \frac{T_k \cdot s_{i,k}}{(T_k+T_{k+1})/2} \text{ and } s_{i,k+1} \to \frac{T_{k+1} \cdot s_{i,k+1}}{(T_k+T_{k+1})/2}.$$

In other embodiments disclosed herein, an analogous approach can be applied to motion compensated PET imaging using (e.g. respiratory) gating. In this case, two successive gate phases $\phi_k$ and $\phi_{k+1}$ are considered, with some motion represented by a motion vector Δr occurring between the two phases. Then a possible formulation of the adjusted edge preservation parameter is $\gamma_{i,j}^{joint}=\sqrt{\lambda_{i,k}(s_i+s_{i+\Delta r})}$.

With reference to FIG. 1, an illustrative medical imaging system 10 is shown. As shown in FIG. 1, the system 10 includes an imaging or image acquisition device 12. In one example, the image acquisition device 12 can comprise a PET imaging device including a PET gantry 13 and an array of radiation detectors 14 (diagrammatically indicated in FIG. 1; typically, the radiation detectors of the PET gantry are arranged as a series of PET detector rings arranged to span an axial FOV). The illustrative image acquisition device 12 is a PET/CT scanner that further includes a computed tomography (CT) gantry 15. A patient table (or bed) 16 is arranged to load a patient into an examination region 17 of the imaging device 12, e.g. into the bore of the CT gantry 15 or into the bore of the PET gantry 13. Commonly, the CT gantry 15 is used to acquire a CT image of the subject that is converted to an attenuation map of the subject. The PET gantry 13 acquires the PET imaging data which is reconstructed using the attenuation map from the CT image to account for radiation absorption in the patient in the PET image reconstruction.

The system 10 also includes a computer or workstation or other electronic data processing device 18 with typical components, such as at least one electronic processor 20, at least one user input device (e.g., a mouse, a keyboard, a trackball, trackpad, and/or the like) 22, and a display device 24 (for example, an LCD display, OLED display, plasma display, or the like). In some embodiments, the display device 24 can be a separate component from the computer 18, and/or may comprise two or more displays. The workstation 18 can also include one or more databases or non-transitory storage media 26 (such as a magnetic disk, RAID, or other magnetic storage medium; a solid state drive, flash drive, electronically erasable read-only memory (EEROM) or other electronic memory; an optical disk or other optical storage; various combinations thereof; or so forth). The display device 24 is configured to display images acquired by the imaging system 10 and typically also to display a graphical user interface (GUI) 28 including various user dialogs, e.g. each with one or more fields, radial selection buttons, et cetera to receive a user input from the user input device 22.

The at least one electronic processor 20 is operatively connected with the one or more databases 26 which stores instructions which are readable and executable by the at least one electronic processor 20 to perform disclosed operations including performing an imaging method or process 100. In some examples, the imaging method or process 100 may be performed at least in part by cloud processing.

Figure 2:
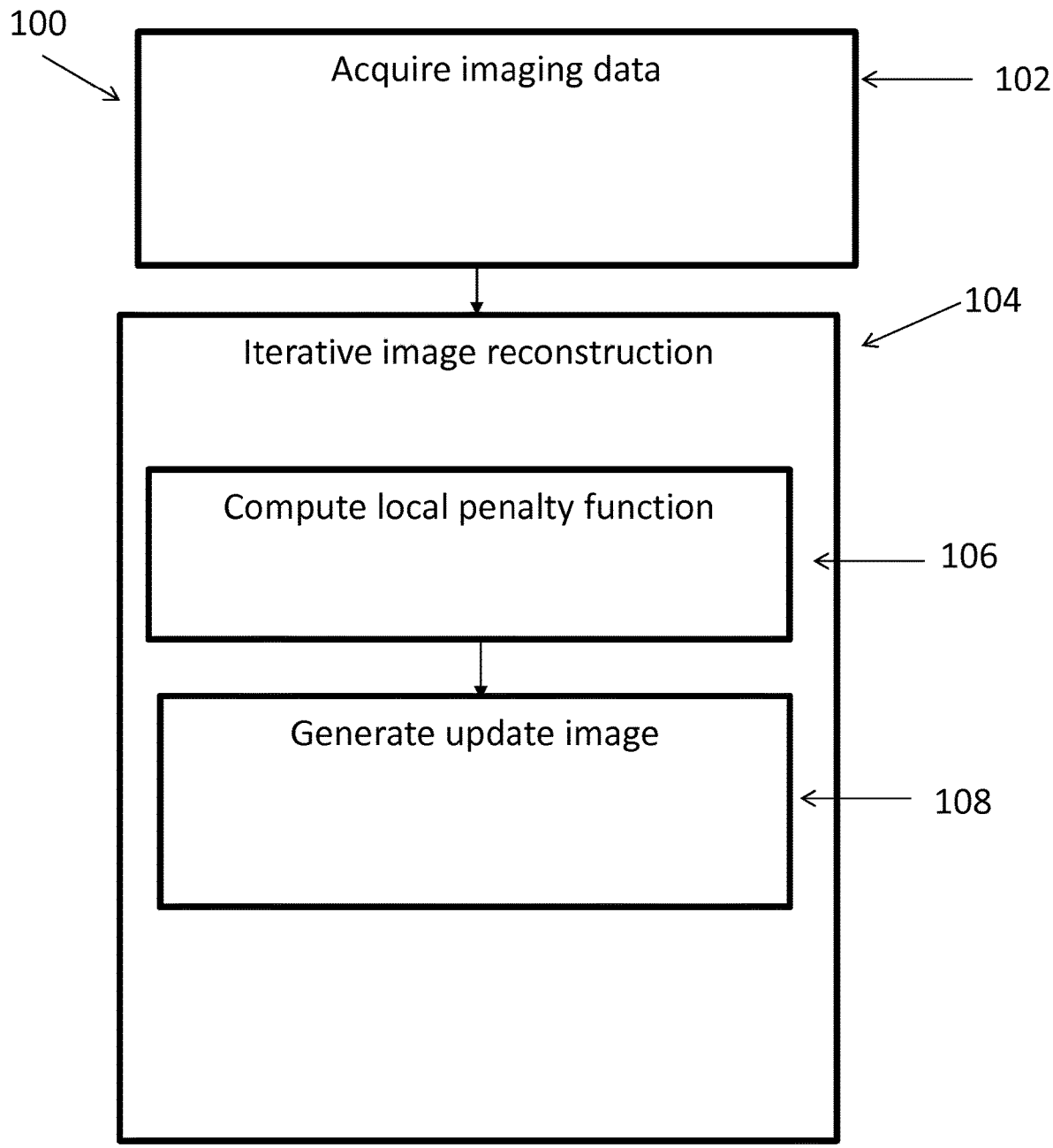
FIGS. 2 and 3 show exemplary flow chart operations of the system of FIG. 1.

With reference to FIG. 2, an illustrative embodiment of the imaging method 100 is diagrammatically shown as a flowchart. At 102, the at least one electronic processor 20 is programmed to receive, other otherwise operate or control the CT/PET imaging device 12 (and more particularly the PET gantry 13) to, acquire PET imaging data on a frame by frame basis for frames along an axial direction with neighboring frames overlapping along the axial direction wherein the frames include at least a volume (k) and a succeeding volume (k+1) at least partially overlapping the volume (k) along the axial direction. At 104, the at least one electronic processor 20 is programmed to generate an image of the volume (k) using an iterative image reconstruction process includes operations 106 and 108. At 106, a local penalty function is computed for suppressing noise over the volume (k) including reducing the value of the local penalty function in an overlap region. At 108, an update image of the volume (k) is generated using imaging data from the volume (k) and further using the local penalty function. Although not illustrated, it will be understood that the iterative image reconstruction 104 may take into account radiation absorption in the subject using an attenuation map generated from a CT image acquired of the subject using the CT gantry 15.

In one embodiment disclosed herein, the local penalty function depends on local geometric sensitivity of the PET imaging device 12 and the value of the local penalty function is reduced in the overlap region by an amount compensating for loss of geometric sensitivity due to axial truncation of the volume (k). An illustrative example is described next, in which the edge-preserving penalty function is a Relative Difference Prior (RDP) and ordered subset expectation maximization (OSEM) reconstruction is used. The update image indexed n+1 for iteration n is suitably written as:

$$\lambda_i^{n+1} = \tag{1}$$

$$\lambda_i^n + \underbrace{\frac{\lambda_i^n}{s_{i,k}} \frac{\partial}{\partial \lambda_i} \left[ \sum_{j=1}^N \left( y_i \log \left( \sum_{j'=1}^P a_{jj'} \lambda_i^n + r_j \right) - \left( \sum_{j'=1}^P a_{jj'} \lambda_i^n + r_j \right) \right) \right]}_{\text{MLE}} -$$

$$\underbrace{\frac{\lambda_i^n}{s_{i,k}} \frac{\partial}{\partial \lambda_i} \left[ \sum \beta_{mi}^* \frac{(\lambda_i - \lambda_m)^2}{\lambda_i + \lambda_m + \gamma_i |\lambda_i - \lambda_m|} \right]}_{\text{local RDP penalty}}$$

where $\lambda_i$ is the estimated activity at the voxel indexed by i, and $$\beta_{mi}^* = \frac{w_m \beta_i}{\sum_{\forall m} w_m}$$

is a local penalty weighting factor, $a_{jj}$, is the system matrix value, $s_{i,k}$ is the geometric sensitivity at voxel i (preferably scaled by the acquisition time if different bed positions have different acquisition times), $y_j$ is a data projection bin, and parameter $\gamma_i > 0$ is the edge preservation parameter and steers the RDP prior. The prior is estimated over local image neighborhood $N_i$ around the voxel i. In general, a larger value of $\gamma_i$ produces greater edge preservation (i.e., reduces the penalty). The value $\gamma_i = 0$ would eliminate edge preservation entirely, and the RDP becomes a quadratic prior.

As disclosed herein, the value of the local penalty function is reduced in the overlap region where bed positions of volumes k and k+1 overlap (and also where bed positions of volumes k−1 and k overlap, if current bed position k is overlapped on both ends). In some suitable embodiments, the local penalty function depends on the local geometric sensitivity $s_{i,k}$ of the PET imaging device 12 for the voxel indexed by i in the image volume of the bed position of volume k. The geometric sensitivity at a voxel i can be viewed as the number of lines of response (LORs) passing through that voxel i. In the portion of volume k that does not overlap either of the neighboring volumes k−1 or k+1, the standard sensitivity can be used, and for the n-th iteration the value $\gamma_i = \gamma_0 \sqrt[n]{\lambda_{i,k}^n \cdot s_{i,k}}$ can be used, where $\gamma_0$ is a constant. However, in the overlap region the penalty is reduced. This is achieved by increasing the value of the edge preservation parameter $\gamma$ in the overlap region by an amount compensating for loss of geometric sensitivity due to axial truncation of the volume k. Thus, a "joint" edge preservation parameter $\gamma_{i,k}^{joint}$ is used, which can be suitably written as $\gamma_{i,k}^{joint} = \gamma_0 \sqrt[n]{\lambda_{i,k}^n \cdot (s_{i,k} + s_{i,k+1})}$ where $s_{i,k+1}$ is the geometric sensitivity for the (same) voxel i in the next-neighboring volume k+1. Again, it is emphasized that this adjustment increases the edge preservation parameter (that is, $\lambda_{i,k}^{joint} > \lambda_{i,k}$) which, due to $\gamma$ being in the denominator of the local RDP penalty of Equation (1), results in a reduction of the local RDP penalty in the overlap region. This reduction in the RDP penalty accounts for the additional data in volume k+1 which means that the noise is lower when the two reconstructed volumes k and k+1 are knitted together in the overlap region, so that a lower penalty can be employed in the overlap region when reconstructing the volume k to achieve a desired noise reduction, and hence the features (edges) are better preserved due to the reduced penalty in the overlap region.

In another embodiment, the local penalty function depends on the total coincidence counts passing through the voxel being penalized, and the value of the local penalty function is reduced in the overlap region by an amount compensating for the total coincidence counts passing through the voxel being penalized in the succeeding volume k+1. The penalty may be formulated in terms of actual local coincidence count statistics, rather than in terms of the geometric sensitivity. This entails replacing the geometric sensitivity s in the above expressions with actual counts. In this case, $\gamma_i = \gamma_0 \sqrt[n]{\lambda_{i,k}^n \cdot C_{i,k}}$ (without overlap adjustment) where $C_{i,k}$ is the count of coincidence events in the dataset for bed position k whose LORs pass through the voxel i. For time-of-flight (TOF) PET, this could be formulated as $\gamma_i = \gamma_0 \sqrt[n]{\lambda_{i,k}^n \cdot \sum_{v=1}^{C_{i,k}} w_v}$ where the index v runs over the $C_{i,k}$ coincidence counts of the dataset for bed position k whose LORs pass through the voxel i, and $w_v$ is the time-of-flight probability that the count indexed by v originated in the voxel i. For the non-TOF case, the joint edge preservation parameter (i.e., providing for overlap adjustment) is $\gamma_{i,k}^{joint} = \gamma_0 \sqrt[n]{\lambda_{i,k}^n \cdot (C_{i,k} + C_{i,k+1})}$ where again analogously the term $C_{i,k+1}$ is the count of coincidence events in the dataset for bed position k+1 whose LORs pass through the (same) voxel i. In this formulation it is even more explicit that the reduced penalty (which again is provided by an increased value of the denominator term $\gamma_{i,k}^{joint}$) accounts for the additional data $C_{i,k+1}$ in volume k+1 which means that the noise is lower when the two reconstructed volumes k and k+1 are knitted together in the overlap region. The equivalent formulation for TOF is $\gamma_{i,k}^{joint} = \gamma_0 \sqrt[n]{\lambda_{i,k}^n \cdot (\sum_{v=1}^{C_{i,k}} w_v + \sum_{v=1}^{C_{i,k+1}} w_v)}$ where the summation $\sum_{v=1}^{C_{i,k+1}} w_v$ is in the dataset for volume k+1.

In the above examples, the reconstruction process 106, 108 includes reconstructing each volume (k) of the imaging data separately from the other volumes (k) of the imaging data into a reconstructed bed position image, and then knitting the bed position images together in image space to generate the final image. In other embodiments, the reconstruction process 106, 108 can include combining the number of counts from all volumes (k) in the imaging data into a total volume; and reconstructing the total volume into a reconstructed image. In this latter embodiment, the local penalty function depends upon $$\gamma_i^{joint} = \gamma_0 \sqrt[n]{\lambda_i^n \cdot (s_{i,k} + s_{i,k+1})}$$

In either embodiment, if the acquisition times for successive bed positions are not all the same, then the reduction of the value of the local penalty function in the overlap region is suitably also scaled based on a ratio of respective acquisition times for the volume (k) and the succeeding volume k+1.

Figure 3:
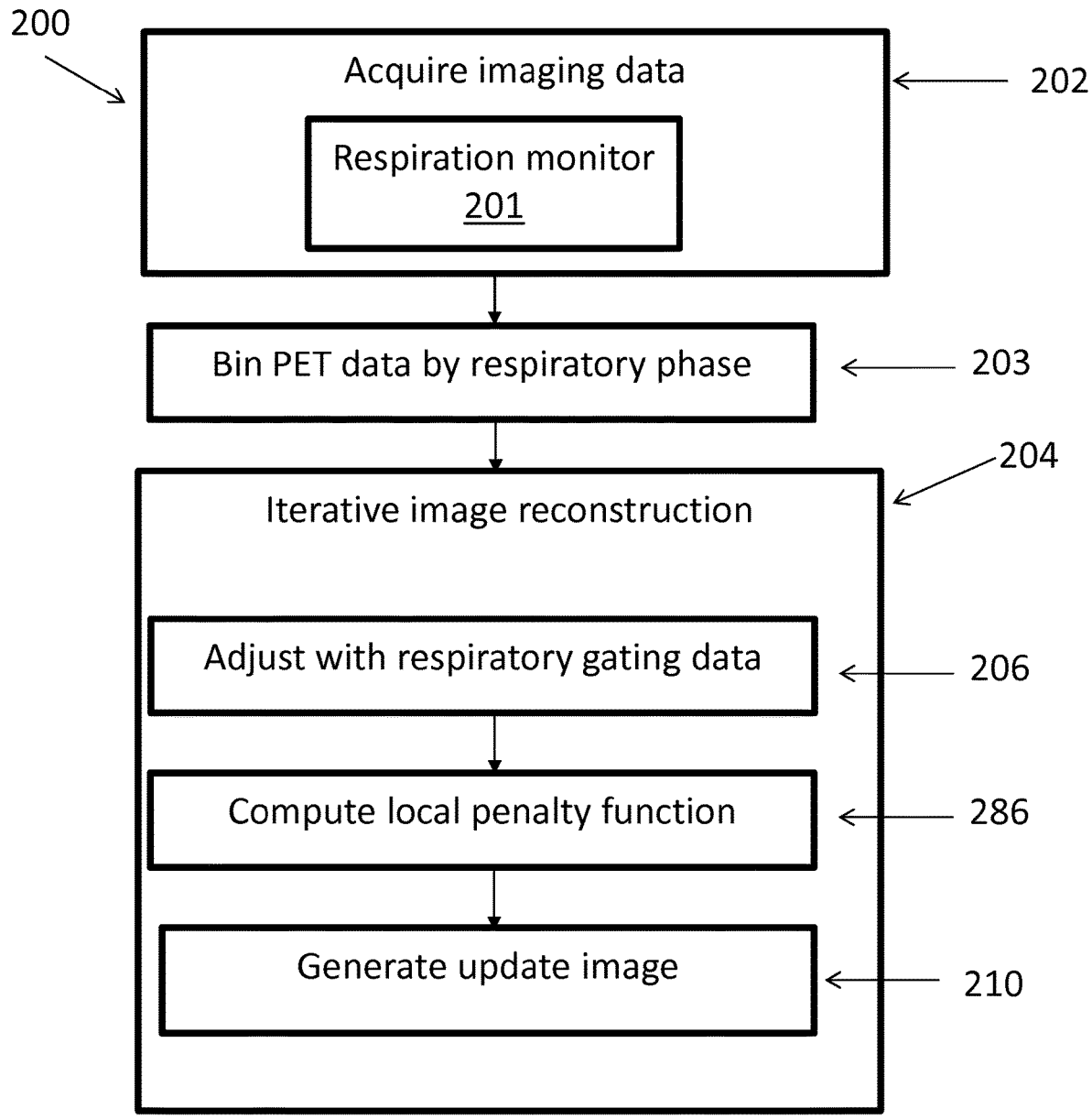

With reference to FIG. 3, an illustrative embodiment of a respiratory-gated imaging method 200 is diagrammatically shown as a flowchart. This is a different application, but the disclosed approach of adjusting the penalty in the (now temporal, rather than spatial/axial) overlap region is analogous. At 202, the at least one electronic processor 20 is programmed to operate or control the PET imaging device 12 to acquire imaging data of a respiring patient. Concurrently with the PET imaging data acquisition, a respiratory gating signal is acquired by a respiration monitor 201 which provides respiratory phase-versus-time information. For example, the respiratory gating signal can be provided by the respiration monitor 201 comprising a respiration monitor belt that measures expansion and contraction of the chest during breathing; or the respiratory gating signal can be provided by the respiration monitor 201 comprising a flow sensor that measures air flow into/out of the mouth and/or nose; or so forth. At 203, the PET data are binned by respiratory phase using the respiratory gating signal. By analogy to the multi-bed position imaging example of FIG. 2, each respiratory phase bin is denoted by index k, and two adjacent respiratory phase bins k and k+1 are adjacent in the respiratory sequence, that is, in each breath interval the respiratory phase k+1 immediately follows the respiratory phase k in time. It will be appreciated that the binning by respiratory phase will result in the PET data acquired over the same respiratory phase k in successive breaths being combined to form the PET data set for respiratory phase bin k; and likewise the PET data acquired over the same respiratory phase k+1 in successive breaths will be combined to form the PET data set for respiratory phase bin k+1; and so forth. Moreover, the bins overlap in time. At 204, the at least one electronic processor 20 is programmed to generating an image of the respiratory phase (k) using an iterative image reconstruction process operating on the acquired PET imaging data that is accumulated in the respiratory phase bin (k) over multiple breaths. The iterative reconstruction 204 includes operations 206, 208, and 210. At 206, the imaging data of each bin is adjusted for respiratory motion detected in the gate phases. This entails shifting the counts of LOR endpoints according to derived motion vectors. For each voxel i, there is an associated motion vector $\Delta r_i$ indicating the movement of the voxel i from its reference position (which may, for example, be designated arbitrarily as its position at bin k=0 so that $\Delta r_{i,k=0}=0$ for all i). At 208, a local penalty function is computed for suppressing noise in the respiratory phase bin (k) including reducing the value of the local penalty function in a temporal overlap region with the respiratory phase bin k+1. At 210, an update image of the respiratory phase bin (k) is generated using imaging data from the respiratory phase bin (k) and further using the local penalty function.

In some embodiments, the adjusting at operation 206 is performed according to:

$$\gamma_{i,k}^{joint} = \gamma_0 \sqrt{f_{i,k}(s_i + s_{i+\Delta r})}.$$

where $\gamma$ is an edge preservation parameter, i is a voxel, $\lambda$ is a greyscale value of the voxel, s is a geometric sensitivity passing through the voxel, and $\Delta r$ is a motion vector between two gate phases $\phi_k$ and $\phi_{k+1}$.

Figure 4:
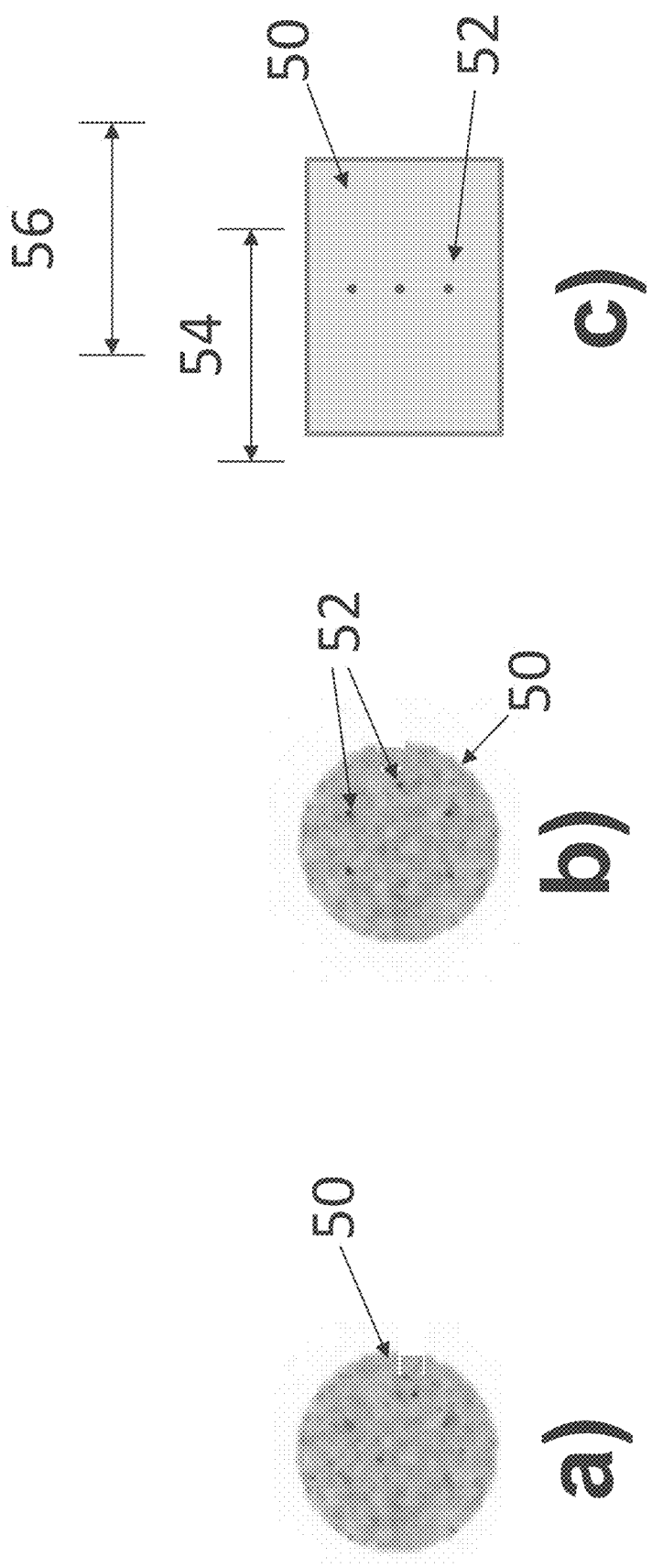
FIGS. 4a-c show a comparison of a standard reconstructed image versus an image reconstructed with the flow chart operations of FIG. 2.

FIG. 4 shows examples of reconstructed images using uniform phantom with six 6 mm diameter spheres in hexagonal pattern located in the center of the overlap region. The figure labeled (a) is an image reconstructed with a standard penalized reconstruction after knitting. The figure labeled (b) is an image reconstructed with a joint penalized reconstruction of the imaging method 100. A side view of the phantom setup is shown in the figure labeled (c). A cylinder phantom 50 is shown with multiple spheres 52 over a first bed position 54 and second bed position 56.

The disclosure has been described with reference to the preferred embodiments. Modifications and alterations may occur to others upon reading and understanding the preceding detailed description. It is intended that the disclosure be construed as including all such modifications and alterations insofar as they come within the scope of the appended claims or the equivalents thereof.

The invention claimed is:

1. A non-transitory computer-readable medium storing instructions readable and executable by a workstation including at least one electronic processor to perform an imaging method, the method comprising:
   receiving imaging data on a frame by frame basis for frames along an axial direction with neighboring frames overlapping along the axial direction wherein the frames include at least a volume (k) and a succeeding volume (k+1) at least partially overlapping the volume (k) along the axial direction; and
   generating an image of the volume (k) using an iterative image reconstruction process in which an iteration of the iterative image reconstruction process includes:
   computing a local penalty function for suppressing noise over the volume (k), wherein the local penalty function depends on the total coincidence counts passing through the voxel being penalized, and the value of the local penalty function is reduced in an overlap region by an amount compensating for the total coincidence counts passing through the voxel being penalized in the succeeding volume k+1; and
   generating an update image of the volume (k) using imaging data from the volume (k) and further using the local penalty function.

2. The non-transitory computer-readable medium of claim 1, wherein the penalty function depends upon $\gamma_i = \gamma_0 \sqrt{\lambda_{i,k}^n \cdot C_{i,k}}$
   where $\gamma$ is an edge preservation parameter of the local penalty function, i indexes a voxel, $\lambda_{i,k}^n$ is the value of the voxel i in the iterative reconstruction of the volume k specifically in the update image n of that iterative reconstruction n; $C_{i,k}$ is the count of coincidence events in the dataset for bed position of volume k whose LORs pass through the voxel i.

3. The non-transitory computer-readable medium of claim 2, wherein the PET imaging device is a time-of-flight imaging device, and
   the penalty function depends upon $\gamma_i = \gamma_0 \sqrt{\lambda_{i,k}^n \cdot \Sigma_{\nu=1}^{C_{i,k}} w_\nu}$
   where $\gamma$ is an edge preservation parameter of the local penalty function, i indexes a voxel, $\lambda_{i,k}^n$ is the value of the voxel i in the iterative reconstruction of the volume k specifically in the update image n of that iterative reconstruction n; $C_{i,k}$ is the count of coincidence events in the dataset for bed position of volume k whose LORs pass through the voxel i; and the index $\nu$ runs over the $C_{i,k}$ coincidence counts of the dataset for bed position k whose LORs pass through the voxel i, and $w_\nu$ is the time-of-flight probability that the count indexed by $\nu$ originated in the voxel i.

4. The non-transitory computer-readable medium of claim 1, wherein the reconstructing includes:
   reconstructing the volume (k) of the imaging data separately from the other volumes (k) of the imaging data into a reconstructed image.

5. The non-transitory computer-readable medium of claim 1, wherein the reconstructing includes:
   combining the number of counts from the volumes (k) in the imaging data into a total volume; and
   reconstructing the total volume into a reconstructed image.

6. The non-transitory computer-readable medium of claim 5, wherein the local penalty function depends upon $\gamma_{i,k}^{joint} = \sqrt{\lambda_{i,k}^n \cdot (s_{i,k} + s_{i,k+1})}$
   where $\gamma$ is an edge preservation parameter of the local penalty function, i indexes a voxel, $\lambda_{i,k}^n$ is the value of the voxel i in the iterative reconstruction of the volume k specifically in the update image n of that iterative reconstruction n, $s_{i,k}$ is the geometric sensitivity of the PET imaging device for voxel i when acquiring data on the volume k and $s_{i,k+1}$ is the geometric sensitivity of the PET imaging device for voxel i when acquiring data on the volume k+1.

7. The non-transitory computer-readable medium of claim 1, wherein the reducing of the value of the local penalty function in the overlap region is scaled based on a ratio of respective acquisition times for the volume (k) and the succeeding volume k+1.

8. An imaging system, comprising:
a positron emission tomography (PET) imaging device; and
at least one electronic processor programmed to:
  receive imaging data on a frame by frame basis for frames along an axial direction with neighboring frames overlapping along the axial direction wherein the frames include at least a volume (k) and a succeeding volume (k+1) at least partially overlapping the volume (k) along the axial direction; and
  generate an image of the volume (k) using an iterative image reconstruction process in which an iteration of the iterative image reconstruction process includes:
    computing a local penalty function for suppressing noise over the volume (k) including reducing the value of the local penalty function in an overlap region, the local penalty function depending on the total coincidence counts passing through the voxel being penalized, and the value of the local penalty function is reduced in the overlap region by an amount compensating for the total coincidence counts passing through the voxel being penalized in the succeeding volume k+1;
    generating an update image of the volume (k) using imaging data from the volume (k) and further using the local penalty function;
wherein $\gamma$ is an edge preservation parameter of the local penalty function, i indexes a voxel, $\lambda_{i,k}^n$ is the value of the voxel i in the iterative reconstruction of the volume k specifically in the update image n of that iterative reconstruction n, and the local penalty function depends upon one of:
(i) $\gamma_i = \gamma_0 \sqrt{\lambda_{i,k}^n \cdot C_{i,k}}$ where $C_{i,k}$ is the count of coincidence events in the dataset for bed position of volume k whose LORs pass through the voxel i, or
(ii) $\gamma_{i,k}^{joint} = \sqrt{\lambda_{i,k}^n \cdot (s_{i,k} + s_{i,k+1})}$ where $s_{i,k}$ is the geometric sensitivity of the PET imaging device for voxel i when acquiring data on the volume k and $s_{i,k+1}$ is the geometric sensitivity of the PET imaging device for voxel i when acquiring data on the volume k+1; and
wherein the reconstructing includes combining the number of counts from the volumes (k) in the imaging data into a total volume, and reconstructing the total volume into a reconstructed image.

9. The system of claim 8, wherein the local penalty function depends upon $\gamma_i = \gamma_0 \sqrt{\lambda_{i,k}^n \cdot C_{i,k}}$.

10. The system of claim 9, wherein the PET imaging device is a time-of-flight imaging device, and
the local penalty function depends upon $\gamma_i = \gamma_0 \sqrt{\lambda_{i,k}^n \cdot \Sigma_{v=1}^{C_{i,k}} w_v}$, where the index v runs over the $C_{i,k}$ coincidence counts of the dataset for bed position k whose LORs pass through the voxel i, and $w_v$ is the time-of-flight probability that the count indexed by v originated in the voxel i.

11. The system of claim 8, wherein the local penalty function depends upon $\gamma_{i,k}^{joint} = \sqrt{\lambda_{i,k}^n \cdot (s_{i,k} + s_{i,k+1})}$.

12. The system of claim 8, wherein the reducing of the value of the local penalty function in the overlap region is scaled based on a ratio of respective acquisition times for the volume (k) and the succeeding volume k+1.

13. An imaging method performed on imaging data on a frame by frame basis for frames along an axial direction with neighboring frames overlapping along the axial direction wherein the frames include at least a volume (k) and a succeeding volume (k+1) at least partially overlapping the volume (k) along the axial direction, the method comprising:
  generating an image of the volume (k) using an iterative image reconstruction process in which an iteration of the iterative image reconstruction process includes:
    computing a local penalty function for suppressing noise over the volume (k) including reducing the value of the local penalty function in an overlap region, the local penalty function depends on local geometric sensitivity of the PET imaging device and the value of the local penalty function is reduced in the overlap region by an amount compensating for loss of geometric sensitivity due to axial truncation of the volume (k);
    generating an update image of the volume (k) using imaging data from the volume (k) and further using the local penalty function;
wherein the reconstructing includes:
reconstructing the volume (k) of the imaging data separately from the other volumes (k) of the imaging data into a reconstructed image;
wherein the local penalty function depends upon $\gamma_{i,k}^{joint} = \sqrt{\lambda_{i,k}^n \cdot (s_{i,k} + s_{i,k+1})}$
where $\gamma$ is an edge preservation parameter of the local penalty function, i indexes a voxel, $\lambda_{i,k}^n$ is the value of the voxel i in the iterative reconstruction of the volume k specifically in the update image n of that iterative reconstruction n, $s_{i,k}$ is the geometric sensitivity of the PET imaging device for voxel i when acquiring data on the volume k and $s_{i,k+1}$ is the geometric sensitivity of the PET imaging device for voxel i when acquiring data on the volume k+1.

14. The imaging method of claim 13, wherein the reducing of the value of the local penalty function in the overlap region is scaled based on a ratio of respective acquisition times for the volume (k) and the succeeding volume k+1.

15. An imaging method performed on imaging data on a frame by frame basis for frames along an axial direction with neighboring frames overlapping along the axial direction wherein the frames include at least a volume (k) and a succeeding volume (k+1) at least partially overlapping the volume (k) along the axial direction, the method comprising:
  generating an image of the volume (k) using an iterative image reconstruction process in which an iteration of the iterative image reconstruction process includes:
    adjusting the imaging data with respiratory gating using two or more gate phases and motion detected in the gate phases according to $\gamma_{i,j}^{joint} = \gamma_0 \sqrt{f_{i,k}(s_i + s_{i+\Delta_r})}$ where $\gamma$ is an edge preservation parameter, i is a voxel, f is a greyscale value of the voxel, s is a geometric sensitivity passing through the voxel, and $\Delta_r$ is a motion vector between two gate phases $\phi_k$ and $\phi k+1$;
    computing a local penalty function for suppressing noise over the volume (k) including reducing the value of the local penalty function in an overlap region;

generating an update image of the volume (k) using imaging data from the volume (k) and further using the local penalty function.

\* \* \* \* \*